United States Patent [19]

Kobayashi

[11] Patent Number: 5,519,157
[45] Date of Patent: May 21, 1996

[54] FLUORINE-CONTAINING ORGANOSILICON COMPOUNDS AND METHOD FOR THEIR PREPARATION

[75] Inventor: Hideki Kobayashi, Chiba, Japan

[73] Assignee: Dow Corning Toray Silicone Co., Ltd., Tokyo, Japan

[21] Appl. No.: 492,408

[22] Filed: Jun. 19, 1995

[30] Foreign Application Priority Data

Jun. 22, 1994 [JP] Japan ..................... 6-163222

[51] Int. Cl.$^6$ ................. C07F 7/08; C07F 7/18
[52] U.S. Cl. ............................................. 556/435
[58] Field of Search ................................ 556/435

[56] References Cited

U.S. PATENT DOCUMENTS

| | | | |
|---|---|---|---|
| 3,580,940 | 5/1971 | Webster | 556/435 |
| 4,089,882 | 5/1978 | Takamizawa et al. | 260/448.2 |
| 4,788,312 | 11/1988 | Paciorek et al. | 556/435 |
| 5,117,026 | 5/1992 | Kishita et al. | 556/435 |
| 5,391,794 | 2/1995 | Jung et al. | 556/435 |
| 5,399,740 | 3/1995 | Jung et al. | 556/435 |

FOREIGN PATENT DOCUMENTS 57-140787  2/1982  Japan.

*Primary Examiner*—Paul F. Shaver
*Attorney, Agent, or Firm*—Timothy J. Troy

[57] ABSTRACT

The present invention relates to fluorine-containing organosilicon compounds and a method for their preparation. The fluorine-containing organosilicon compounds of this invention have low surface tension, excellent solvent resistance, water-repellency, and oil-repellency characteristics. The fluorine-containing organosilicon compounds of this invention also do not easily depolymerize by hydrolysis under acidic and alkaline conditions.

20 Claims, No Drawings

FLUORINE-CONTAINING ORGANOSILICON COMPOUNDS AND METHOD FOR THEIR PREPARATION

BACKGROUND OF THE INVENTION

The present invention relates to novel fluorine-containing organosilicon compounds and a method for their preparation. Organopolysiloxanes which contain fluorine atoms in their molecules have a low surface tension and are excellent in water-repelling and oil-repelling characteristics, and solvent resistance, and they have been used as a surface-modifying agents for a variety of base materials. These type of organopolysiloxanes are generally prepared by the condensation polymerization of a fluorine-containing organosilicon compound having a hydrolyzable group. Generally, the fluorine-containing organosilicon compounds have been, for example, a compound having the formula:

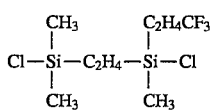

and a compound having the formula:

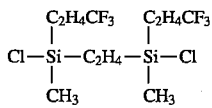

These types of compounds have been disclosed, for example, Japanese Patent Application Laid Open Nos. 4-59785 (59,785/1992) and 4-59783 (59,783/1992). However, fluorine-containing organopolysiloxanes prepared from these types of fluorine-containing organosilicon compounds are readily depolymerized by hydrolysis under acidic and alkaline conditions and thus their applications have been limited.

SUMMARY OF THE INVENTION

The present invention relates to novel fluorine-containing organosilicon compounds and a method for their preparation.

It is an object of the present invention to provide novel fluorine-containing organosilicon compounds having low surface tension.

It is another object of the present invention to provide novel fluorine-containing organosilicon compounds which have excellent solvent resistance, water-repellency, and oil-repellency characteristics.

It is a further object of the present invention to provide an efficient method of preparing fluorine-containing organosilicon compounds having low surface tension.

It is a further object of this invention to produce fluorine-containing organosilicon compounds which do not easily depolymerize by hydrolysis under acidic and alkaline conditions.

DETAILED DESCRIPTION OF THE INVENTION

The present invention relates to fluorine-containing organosilicon compounds having the formula:

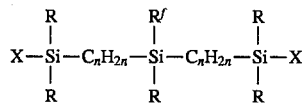

wherein R is a monovalent hydrocarbon group having at least one carbon atom, $R^f$ is a monovalent organic group having at least two —$CF_2$— groups and having at least 4 carbon atoms, X is selected from a halogen atom or an alkoxy group having from 1 to 10 carbon atoms, and n has a value of 2 or 3.

In the above formula, R is a monovalent hydrocarbon group having at least one carbon atom. Groups suitable as R include alkyl groups such as methyl, ethyl, propyl, butyl, octyl, decyl, and hexadecyl, and aryl groups such as phenyl and styryl. Preferred as R are methyl or phenyl. The group $R^f$ is a monovalent organic group having at least two —$CF_2$— groups and having at least 4 carbon atoms. Preferably $R^f$ is selected from the group consisting of —$(CH_2)_x(CF_2)_yF$, —$(CH_2)_x(CF_2)_yCF(CF_3)_2$, —$(CH_2)_xO(CF_2)_yF$, —$(CH_2)_xO(CH_2)_z(CF_2)_yF$, and a compound having the formula:

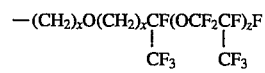

wherein x and y are integers having a value of at least 2, and z is an integer having a value of 1 and 20. It is highly preferred that $R^f$ is a group having the formula —$(CH_2)_x(CF_2)_yF$ wherein x and y are as defined as above. The group X above is a halogen atom or an alkoxy group having from 1 to 10 carbon atoms. For example, X can be a chlorine atom or bromine atom. Alkoxy groups include groups such as methoxy, ethoxy, and propoxy. The value of n is 2 or 3.

Preferred fluorine-containing organosilicon compounds are selected from the group consisting of:

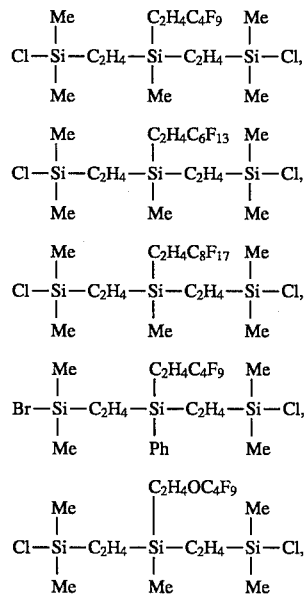

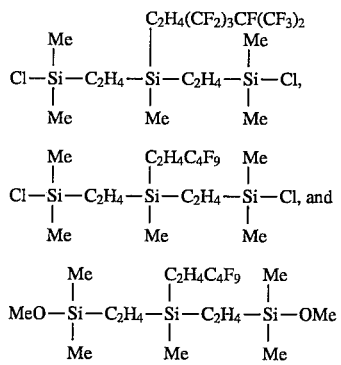

wherein Me denotes methyl, and Ph denotes phenyl.

The present invention further relates to a method for the preparation of fluorine-containing organosilicon compounds comprising the step of: (I) reacting: (A) a dihydrosilane having the formula R'SiH$_2$R wherein R is a monovalent hydrocarbon group having at least one carbon atom, and R' is a monovalent organic group having at least two —CF$_2$— groups and having at least 4 carbon atoms; and (B) an organosilane having the formula R'SiR$_2$X wherein R is a monovalent hydrocarbon group having at least one carbon atom, R' is selected from a vinyl group or an allyl group, and X is selected from a halogen atom or an alkoxy group having from 1 to 10 carbon atoms; in the presence of (C) a catalyst.

In Component (A) of the method of the present invention, R and R' in the above formulas are as defined above including preferred embodiments thereof. Preferred as Component (A) are dihydrosilanes selected from the group consisting of C$_4$F$_9$C$_2$H$_4$SiMeH$_2$, C$_6$F$_{13}$C$_2$H$_4$SiMeH$_2$, C$_8$F$_{17}$C$_2$H$_4$SiMeH$_2$, C$_4$F$_9$C$_2$H$_4$SiPhH$_2$, (CF$_3$)$_2$CF(CF$_2$)$_3$C$_2$H$_4$SiMeH$_2$, F[CF(CF$_3$)CF$_2$O]$_3$CF(CF$_3$)C$_2$H$_4$OC$_3$H$_6$SiMeH$_2$, F[CF(CF$_3$)CF$_2$O]$_5$CF(CF$_3$)C$_3$H$_6$OC$_2$H$_4$SiMeH$_2$, F(CF$_2$)$_4$O(CH$_2$)$_3$SiMeH$_2$, C$_4$F$_9$CH$_2$OC$_2$H$_4$SiMeH$_2$, C$_6$F$_{13}$CH$_2$OC$_2$H$_4$SiMeH$_2$, and C$_8$F$_{17}$CH$_2$OC$_2$H$_4$SiMeH$_2$ wherein Me denotes methyl and Ph denotes phenyl.

The dihydrosilanes of Component (A) can be prepared by the reduction of the halogen atoms of halosilanes having the formula R'SiRZ$_2$ where R and R' are as defined above, by conventional methods. Reducing agents which can be used include, for example, lithium aluminum hydride, sodium aluminum hydride, lithium hydride, Al(BH$_4$)$_3$, and sodium dihydrobis (methoxyethoxy)aluminate. The amount of reducing agent added must be sufficient to provide 2 moles of hydride per mole of the halosilane above. Ordinarily, 1.05–2 times this amount (the amount corresponding to 2 moles of hydride) are used. Any excess reducing agent can be deactivated by the addition of water, alcohol, or ethyl acetate. Among these, water is preferred because it can be removed easily. Furthermore, it is preferable that this reduction reaction be carried out in the presence of an organic solvent including ethers such as ethyl ether, tetrahydrofuran, dibutyl ether, and diisopropyl ether, alkanes such as hexane or heptane, or aromatic hydrocarbons such as benzene or toluene. The reaction temperature is generally in the range of 0°–80° C. After the reaction, salts formed as by-products together with the reaction products can be removed by filtration or water washing.

In the organosilane of Component (B) in the method of the present invention, R and X in the formula for (B) above are as described hereinabove for the organosilicon compounds of this invention, including preferred embodiments thereof, and R' is a vinyl group or an allyl group. Organosilanes suitable as (B) include CH$_2$=CHSiMe$_2$Cl, CH$_2$=CHSiMe$_2$OMe, CH$_2$=CHSiMe$_2$OEt, CH$_2$=CHSiMePhCl, and CH$_2$=CHCH$_2$SiMe$_2$Cl wherein Me denotes methyl, Et denotes ethyl, and Ph denotes phenyl.

The catalyst of Component (C) in the method of this invention is a catalyst for the promotion of the addition reaction between the silicon-bonded hydrogen atoms of Component (A) and the vinyl group or the allyl group of Component (B). Catalysts suitable for the hydrosilylation reaction include platinum catalysts, rhodium catalysts, and palladium catalysts. Platinum catalysts are preferred as (C) in the method of this invention. Preferred platinum catalysts include platinum black, platinum supported on silica micropowder, platinum supported on carbon powder, chloroplatinic acid, an alcohol solution of chloroplatinic acid, a complex of platinum and divinyltetramethyldisiloxane, and complexes of platinum and olefins. The amount of (C) added is generally sufficient to provide an amount of platinum metal in the range of 0.1–1,000 parts by weight per 1 million parts by weight of Components (A) and (B).

The method of the present invention is an addition reaction of Components (A) and (B) in the presence of Component (C). The sequence of the addition of these components is not restricted. For example, a mixture of Components (B) and (C) can be heated and stirred, then Component (A) can be slowly added to the heated mixture. Also, a mixture of Components (A) and (C) can be heated and stirred, then Component (B) can be slowly added to the heated mixture. Furthermore, a mixture of Components (A) and (B) can be heated and stirred, then Component (C) can be slowly added to the mixture. Finally, a mixture of Components (A), (B), and (C) can be heated and stirred.

The method of the present invention can be carried out in the presence of an organic solvent. Examples of organic solvents that can be used include toluene, xylene and other aromatic hydrocarbon solvents, hexane, heptane, octane, nonane and other aliphatic hydrocarbon solvents, cyclohexane, cycloheptane, cyclooctane and other alicyclic hydrocarbon solvents, trifluoromethylbenzene, 1,3-bis(trifluoromethyl)benzene, methylpentafluorobenzene and other fluorine atom-containing aromatic hydrocarbon solvents.

There are no special restrictions on the reaction conditions in the method of the present invention. If the addition reaction is carried out under ambient pressure, the reaction temperature is generally from room temperature to the boiling point of Component (A) or (B) or the boiling point of the organic solvent used. Also, if the boiling points of Component (A), Component (B) and the organic solvent used are relatively low, it is possible to carry out the addition reaction under pressure.

The fluorine-containing organic silicon compounds of the present invention have low surface tension and have excellent solvent resistance, water-repelling and oil-repelling characteristics. Furthermore, the silicon-atom-bonded halogen atoms or alkoxy groups bonded to the terminals of molecular chains can be converted to silicon-atom-bonded hydrogen atoms, hydroxyl groups, acetoxy groups, aminoxy groups and other reactive groups by conventional, known methods. The fluorine-containing organic silicon compounds having reactive groups at the terminals obtained in this manner are useful as surface-treating agents or surface-modifying agents. Moreover, by the hydrolysis of the fluorine-containing organosilicon compounds of the present invention by the conventional methods, fluorine-containing organopolysiloxanes can be obtained. Because the organopolysiloxanes obtained in this manner have high fluorine atom content, they are excellent in interfacial characteristics, heat resistance, and solvent resistance. Furthermore, because they have silethylene units or silpropylene units on the main chains, they depolymerize easily under acidic or alkaline conditions. In the examples hereinbelow, Me is a methyl group.

EXAMPLE 1

In a 1,000-cc flask, 10.45 g of lithium aluminum hydride and 200 g of ethyl ether were added. While the mixture was stirred, 183 g of a dichlorosilane having the formula $C_4F_9CH_2CH_2SiMeCl_2$ were added dropwise into this mixture at room temperature. After the dropwise addition was completed, this mixture was heated and refluxed for 1 hour. After refluxing, water was added to the reaction product to deactivate the excess lithium aluminum hydride, water was added to dissolve the salt, and the organic layer was washed with water. Next, this reaction product was dehydrated by adding anhydrous magnesium sulfate to the organic solvent. It was then filtered and distilled to obtain a dihydrosilane represented by the formula $C_4F_9CH_2CH_2SiMeH_2$ with a boiling point of 116° C.

In a 500-cc flask, 121 g (1 mole) of dimethylvinylchlorosilane and a solution of a complex of platinum and divinyltetramethyldisiloxane were added in quantities such that the content of the platinum metal was about 200 ppm. This mixture was then heated to 60° C. To this mixture, 92 g (0.3 moles) of the dihydrosilane obtained above was added dropwise. After the dropwise addition was complete, the mixture was heated to reflux to cause mixing for 4 hours. After mixing, it was distilled under a reduced pressure to obtain a liquid reaction product. Fourier transform infrared absorption (FT-IR hereinafter) analysis, $^{29}$Si nuclear magnetic resonance ($^{29}$Si-NMR hereinafter) analysis, and $^{13}$C nuclear magnetic resonance ($^{13}$C-NMR hereinafter) analysis were conducted on the obtained reaction product. From these analytical results, it was found that the reaction product obtained was a fluorine-containing organosilicon compound having the formula:

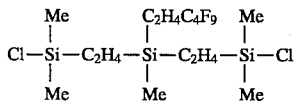

The refractive index of this fluorine-containing organic silicon compound at 25° C. was 1.4152, and its boiling point was 164°–166° C./10 mm Hg.

EXAMPLE 2

In a 500-cc flask, 81 g (0.6 moles) of allyldimethylchlorosilane and a solution of a complex of platinum and divinyltetramethyldisiloxane were added in quantities such that the content of the platinum metal was about 200 ppm. This was heated to 60° C. To this mixture, 98 g (0.2 moles) of a dihydrosilane having the formula $C_8F_{17}CH_2CH_2SiMeH_2$ (obtained by the same method as that in Example 1) were added dropwise. After the dropwise addition was complete, the mixture was heated to reflux to cause mixing for 4 hours. After mixing, it was distilled under a reduced pressure to obtain a liquid reaction product. FT-IR analysis, the $^{29}$Si-NMR analysis and the $^{13}$C-NMR analysis were conducted on the reaction product. From these analytical results, it was found that the reaction product obtained was a fluorine-containing organosilicon compound having the formula:

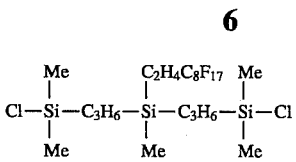

That which is claimed is:

1. An organosilicon compound having the formula:

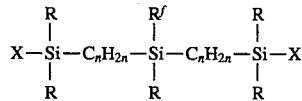

wherein R is a monovalent hydrocarbon group having at least one carbon atom, R$^f$ is a monovalent organic group having at least two —CF$_2$— groups and having at least 4 carbon atoms, X is selected from a halogen atom or an alkoxy group having from 1 to 10 carbon atoms, and n has a value of 2 or 3.

2. A compound according to claim 1, wherein R is selected from alkyl groups or aryl groups.

3. A compound according to claim 1, wherein R is selected from methyl or phenyl.

4. A compound according to claim 1, wherein R$^f$ is selected from the group consisting of —(CH$_2$)$_x$(CF$_2$)$_y$F, —(CH$_2$)$_x$(CF$_2$)$_y$CF(CF$_3$)$_2$, —(CH$_2$)$_x$O(CF$_2$)$_y$F, —(CH$_2$)$_x$O(CH$_2$)$_z$(CF$_2$)$_y$F, and a compound having the formula:

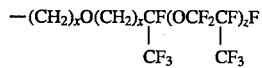

wherein x and y are integers having a value of at least 2, and z is an integer having a value of 1 and 20.

5. A compound according to claim 4, wherein R$^f$ is a group having the formula —(CH$_2$)$_x$(CF$_2$)$_y$F wherein x and y are as defined as above.

6. A compound according to claim 1, wherein X is selected from chlorine, bromine, methoxy, ethoxy, or propoxy.

7. A compound according to claim 1, wherein the fluorine-containing organosilicon compound is selected from the group consisting of:

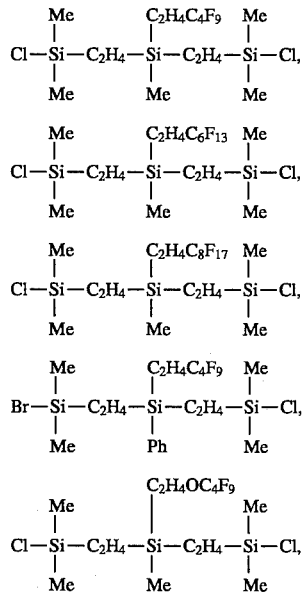

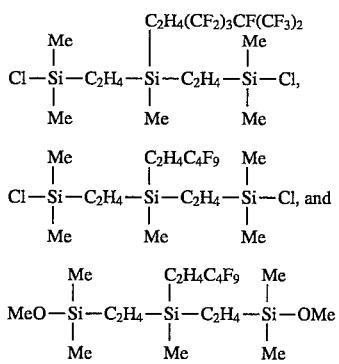

wherein Me denotes methyl, and Ph denotes phenyl.

8. A method for the preparation of organosilicon compounds comprising the step of:
(I) reacting:
(A) a dihydrosilane having the formula:

R$^f$SiH$_2$R wherein R is a monovalent hydrocarbon group having at least one carbon atom, and R$^f$ is a monovalent organic group having at least two —CF$_2$— groups and having at least 4 carbon atoms; and
(B) an organosilane having the formula

R'SiR$_2$X wherein R is as defined above, R' is selected from a vinyl group or an allyl group, and X is selected from a halogen atom or an alkoxy group having from 1 to 10 carbon atoms; in the presence of
(C) a catalyst.

9. A method according to claim 8, wherein R is selected from alkyl groups or aryl groups.

10. A method according to claim 8, wherein R is selected from methyl or phenyl.

11. A method according to claim 8, wherein R$^f$ is selected from the group consisting of —(CH$_2$)$_x$(CF$_2$)$_y$F, —(CH$_2$)$_x$(CF$_2$)$_y$CF(CF$_3$)$_2$, —(CH$_2$)$_x$O(CF$_2$)$_y$F, —(CH$_2$)$_x$O(CH$_2$)$_z$(CF$_2$)$_y$F, and a compound having the formula:

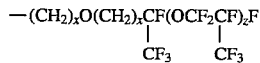

wherein x and y are integers having a value of at least 2, and z is an integer having a value of 1 and 20.

12. A method according to claim 11, wherein R$^f$ is a group having the formula —(CH$_2$)$_x$(CF$_2$)$_y$F wherein x and y are as defined as above.

13. A method according to claim 8 wherein (A) is selected from the group consisting of C$_4$F$_9$C$_2$H$_4$SiMeH$_2$, C$_6$F$_{13}$C$_2$H$_4$SiMeH$_2$, C$_8$F$_{17}$C$_2$H$_4$SiMeH$_2$, C$_4$F$_9$C$_2$H$_4$SiPhH$_2$, (CF$_3$)$_2$CF(CF$_2$)$_3$C$_2$H$_4$SiMeH$_2$, F[CF(CF$_3$)CF$_2$O]$_3$CF(CF$_3$)C$_2$H$_4$OC$_3$H$_6$SiMeH$_2$, F[CF(CF$_3$)CF$_2$O]$_5$CF(CF$_3$)C$_3$H$_6$OC$_2$H$_4$SiMeH$_2$, F(CF$_2$)$_4$O(CH$_2$)$_3$SiMeH$_2$, C$_4$F$_9$CH$_2$OC$_2$H$_4$SiMeH$_2$, C$_6$F$_{13}$CH$_2$OC$_2$H$_4$SiMeH$_2$, and C$_8$F$_{17}$CH$_2$OC$_2$H$_4$SiMeH$_2$ wherein Me denotes methyl and Ph denotes phenyl.

14. A method according to claim 8, wherein X is selected from chlorine, bromine, methoxy, ethoxy, or propoxy.

15. A method according to claim 8, wherein (B) is selected from CH$_2$=CHSiMe$_2$Cl, CH$_2$=CHSiMe$_2$OMe, CH$_2$=CHSiMe$_2$OEt, CH$_2$=CHSiMePhCl, or CH$_2$=CHCH$_2$SiMe$_2$Cl wherein Me denotes methyl, Et denotes ethyl, and Ph denotes phenyl.

16. A method according to claim 8, wherein (C) is selected from platinum catalysts, rhodium catalysts, or palladium catalysts.

17. A method according to claim 16, wherein (C) is a platinum catalyst.

18. A method according to claim 17, wherein the platinum catalyst is selected from platinum black, platinum supported on silica micropowder, platinum supported on carbon powder, chloroplatinic acid, an alcohol solution of chloroplatinic acid, a complex of platinum and divinyltetramethyldisiloxane, or complexes of platinum and olefins.

19. A method according to claim 8, wherein the reaction mixture of (I) further comprises an organic solvent.

20. A method according to claim 19, wherein the organic solvent is selected from toluene, xylene, hexane, heptane, octane, nonane, cyclohexane, cycloheptane, cyclooctane, trifluoromethylbenzene, 1,3-bis(trifluoromethyl)benzene, or methylpentafluorobenzene.

* * * * *